US011779394B2

(12) United States Patent
Baril

(10) Patent No.: US 11,779,394 B2
(45) Date of Patent: Oct. 10, 2023

(54) SINGLE-SIDED LOW PROFILE END EFFECTOR FOR BIPOLAR PENCIL

(71) Applicant: Covidien LP, Mansfield, MA (US)

(72) Inventor: Jacob Baril, North Haven, CT (US)

(73) Assignee: Covidien LP, Mansfield, MA (US)

(*) Notice: Subject to any disclaimer, the term of this patent is extended or adjusted under 35 U.S.C. 154(b) by 871 days.

(21) Appl. No.: 16/776,922

(22) Filed: Jan. 30, 2020

(65) Prior Publication Data
US 2021/0236201 A1 Aug. 5, 2021

(51) Int. Cl.
*A61B 18/14* (2006.01)
*A61B 18/16* (2006.01)

(52) U.S. Cl.
CPC .......... *A61B 18/16* (2013.01); *A61B 18/1402* (2013.01); *A61B 2018/144* (2013.01)

(58) Field of Classification Search
CPC . A61B 18/1402; A61B 18/16; A61B 18/1206; A61B 18/1233; A61B 18/14; A61B 18/1482; A61B 2018/1412; A61B 2018/00178; A61B 2018/126; A61B 2018/00077; A61B 2018/00601; A61B 2018/1405; A61B 2018/144; A61B 2018/162; A61B 2018/167; A61B 17/0218; A61B 17/3494; A61B 17/3423; A61B 2017/00951; A61B 2017/345; A61B 2017/346; A61B 2017/3464; A61B 2090/08021; A61B 2090/036; A61B 90/02; A61B 90/08

See application file for complete search history.

(56) References Cited

U.S. PATENT DOCUMENTS

| 2,022,065 A | 11/1935 | Wappler |
| 2,047,535 A | 7/1936 | Wappler |
| 3,516,412 A | 6/1970 | Ackerman |
| 3,886,944 A | 6/1975 | Jamshidi |
| 4,014,343 A * | 3/1977 | Esty .................. A61B 18/1402 606/49 |
| 4,161,950 A | 7/1979 | Doss et al. |
| 4,196,734 A | 4/1980 | Harris |
| 4,198,957 A | 4/1980 | Cage et al. |
| 4,485,810 A | 12/1984 | Beard |
| 4,534,347 A | 8/1985 | Taylor |

(Continued)

*Primary Examiner* — Khadijeh A Vahdat
(74) *Attorney, Agent, or Firm* — Carter, DeLuca & Farrell LLP

(57) ABSTRACT

An electrode assembly for an electrosurgical pencil includes an insulative core configured to support an active wire around a peripheral surface thereof, the active wire electrically couples to an active pin that inserts into a distal end of the pencil. A ground electrode is operably coupled about the insulative core and inserts within the distal end of the electrosurgical pencil. An insulative material is disposed between the active pin and the ground electrode and is configured to at least partially encapsulate and electrically isolate the active pin from the ground electrode. A first hypotube is disposed atop the insulative core and extends along between the ground electrode and the insulative core, the first hypotube encapsulates the active wire to insulate the active wire from the ground electrode. A second hypotube is operably engaged to a proximal end of the insulative material and is configured to encapsulate the active pin.

20 Claims, 6 Drawing Sheets

(56) References Cited

U.S. PATENT DOCUMENTS

| | | |
|---|---|---|
| 4,622,966 A | 11/1986 | Beard |
| 4,633,880 A | 1/1987 | Osypka et al. |
| 4,862,890 A | 9/1989 | Stasz et al. |
| 5,013,312 A | 5/1991 | Parins et al. |
| 5,085,659 A | 2/1992 | Rydell |
| 5,300,068 A | 4/1994 | Rosar et al. |
| 5,360,428 A | 11/1994 | Hutchinson, Jr. |
| 5,441,499 A | 8/1995 | Fritzsch |
| 5,531,744 A | 7/1996 | Nardella et al. |
| 5,536,267 A | 7/1996 | Edwards et al. |
| 5,599,295 A | 2/1997 | Rosen et al. |
| 5,599,346 A | 2/1997 | Edwards et al. |
| 5,611,798 A | 3/1997 | Eggers |
| 5,752,951 A * | 5/1998 | Yanik ............ A61B 18/1445 606/41 |
| 6,027,501 A | 2/2000 | Goble et al. |
| 6,217,528 B1 | 4/2001 | Koblish et al. |
| 6,494,881 B1 | 12/2002 | Bales et al. |
| 6,530,924 B1 | 3/2003 | Ellman et al. |
| 6,533,781 B2 | 3/2003 | Heim et al. |
| 6,752,767 B2 | 6/2004 | Turovskiy et al. |
| 7,033,354 B2 | 4/2006 | Keppel |
| 7,371,234 B2 | 5/2008 | Young |
| 7,399,299 B2 | 7/2008 | Daniel et al. |
| 7,419,488 B2 | 9/2008 | Ciarrocca et al. |
| 7,846,108 B2 | 12/2010 | Turovskiy et al. |
| 7,846,158 B2 | 12/2010 | Podhajsky |
| 8,137,345 B2 | 3/2012 | McNall, III et al. |
| 8,968,301 B2 | 3/2015 | Weber |
| 9,060,765 B2 | 6/2015 | Rencher et al. |
| 9,358,065 B2 | 6/2016 | Ladtkow et al. |
| 9,445,863 B2 | 9/2016 | Batchelor et al. |
| 9,775,665 B2 | 10/2017 | Ellman |
| 9,993,287 B2 | 6/2018 | Sartor et al. |
| 10,045,761 B2 | 8/2018 | Weber |
| 10,376,314 B2 | 8/2019 | van der Weide et al. |
| 10,433,898 B2 | 10/2019 | Borgmeier et al. |
| 10,433,899 B2 | 10/2019 | Borgmeier et al. |
| 10,531,917 B2 | 1/2020 | Johnson et al. |
| 2005/0070895 A1 | 3/2005 | Ryan et al. |
| 2005/0283149 A1 | 12/2005 | Thorne et al. |
| 2007/0078454 A1 | 4/2007 | McPherson |
| 2007/0118110 A1 | 5/2007 | Girard et al. |
| 2007/0149966 A1 | 6/2007 | Dahla et al. |
| 2007/0179494 A1 | 8/2007 | Faure |
| 2007/0219546 A1 | 9/2007 | Mody et al. |
| 2007/0260240 A1 | 11/2007 | Rusin |
| 2007/0265609 A1 | 11/2007 | Thapliyal et al. |
| 2008/0281323 A1 | 11/2008 | Burbank et al. |
| 2009/0306642 A1 | 12/2009 | Vankov |
| 2019/0083172 A1 | 3/2019 | Ladtkow et al. |
| 2019/0192214 A1* | 6/2019 | Weber ............ A61B 18/1445 |

* cited by examiner

SINGLE-SIDED LOW PROFILE END EFFECTOR FOR BIPOLAR PENCIL

BACKGROUND

Technical Field

The present disclosure relates generally to electrosurgical instruments and, more particularly, to an electrosurgical bipolar pencil configured for bipolar resection.

Background of Related Art

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical pencil, which transfer radio-frequency (RF) electrical or electrosurgical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical coagulation, electrosurgical sealing, electrosurgical cutting, and/or electrosurgical fulguration or, in some instances, an electrosurgical blend thereof.

In particular, electrosurgical fulguration includes the application of an electric spark to biological tissue, for example, human flesh or the tissue of internal organs, without significant cutting. The spark is produced by bursts of radio-frequency electrical or electrosurgical energy generated from an appropriate electrosurgical generator. Coagulation is defined as a process of desiccating tissue wherein the tissue cells are ruptured and dehydrated/dried. Electrosurgical cutting/dissecting, on the other hand, includes applying an electrical spark to tissue in order to produce a cutting, dissecting and/or dividing effect. Blending includes the function of cutting/dissecting combined with the production of a hemostasis effect. Meanwhile, sealing/hemostasis is defined as the process of liquefying the collagen in the tissue so that it forms into a fused mass.

As used herein the term "electrosurgical pencil" is intended to include instruments that have a handpiece which is attached to an active electrode and that is used to cauterize, coagulate and/or cut tissue. Typically, the electrosurgical pencil may be operated by a handswitch or a foot switch.

As mentioned above, the handpiece of the electrosurgical pencil is connected to a suitable electrosurgical energy source (e.g., generator) that produces the radio-frequency electrical energy necessary for the operation of the electrosurgical pencil. In general, when an operation is performed on a patient with an electrosurgical pencil in a monopolar mode, electrical energy from the electrosurgical generator is conducted through the active electrode to the tissue at the site of the operation and then through the patient to a return electrode. The return electrode is typically placed at a convenient place on the patient's body and is attached to the generator by a conductive material. Typically, the surgeon activates the controls on the electrosurgical pencil to select the modes/waveforms to achieve a desired surgical effect. Typically, the "modes" relate to the various electrical waveforms, e.g., a cutting waveform has a tendency to cut tissue, a coagulating wave form has a tendency to coagulate tissue, and a blend wave form tends to be somewhere between a cut and coagulate wave from. The power or energy parameters are typically controlled from outside the sterile field which requires an intermediary like a circulating nurse to make such adjustment.

When an operation is performed on a patient with an electrosurgical pencil in a bipolar mode, the electrode face includes at least one pair of bipolar electrodes and electrical energy from the electrosurgical generator is conducted through tissue between the pair of bipolar electrodes.

A typical electrosurgical generator has numerous controls for selecting an electrosurgical output. For example, the surgeon can select various surgical "modes" to treat tissue: cut, blend (blend levels 1-3), low cut, desiccate, fulgurate, spray, etc. The surgeon also has the option of selecting a range of power settings typically ranging from 1-300 W. As can be appreciated, this gives the surgeon a great deal of variety when treating tissue. Surgeons typically follow preset control parameters and stay within known modes and power settings and electrosurgical pencils include simple and ergonomically friendly controls that are easily selected to regulate the various modes and power settings Electrosurgical instruments are typically configured such that power output can be adjusted without the surgeon having to turn his or her vision away from the operating site and toward the electrosurgical generator.

SUMMARY

As used herein, the term "distal" refers to the portion that is described which is further from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

Provided in accordance with aspects of the present disclosure is an electrode assembly for an electrosurgical pencil that includes an insulative core configured to support an active wire around at least a portion of a peripheral surface thereof, the active wire electrically coupled to an active pin adapted for insertion within a distal end of the electrosurgical pencil. A ground electrode is operably coupled about the insulative core and is adapted for insertion within the distal end of the electrosurgical pencil. An insulative material is disposed between the active pin and the ground electrode and is configured to at least partially encapsulate and electrically isolate the active pin from the ground electrode along a partial length thereof. A first hypotube is disposed atop the insulative core and extends along a length thereof between the ground electrode and the insulative core, the first hypotube encapsulating the active wire to insulate the active wire from the ground electrode along a length thereof. A second hypotube is operably engaged to a proximal end of the insulative material and is configured to at least partially encapsulate the active pin.

In aspects according to the present disclosure, the insulative core includes a cuff adapted to seat the active wire therein. In other aspects according to the present disclosure, a leading edge of the ground electrode is spaced from the peripheral surface of the insulative core to define a gap therebetween configured to electrically isolate the active wire and the ground electrode during activation to avoid arcing.

In aspects according to the present disclosure, the first hypotube defines an opening at a distal end thereof configured to expose and guide the active wire into the cuff defined in the insulative core.

In aspects according to the present disclosure, the insulative core is made from ceramic. In other aspects according to the present disclosure, the active wire is made from tungsten or stainless steel. In still other aspects according to the present disclosure, the ground electrode extends along a length of the insulative core. In yet other aspects according to the present disclosure, the ground electrode is made from a stamped electrically conductive material.

In aspects according to the present disclosure, the insulative material electrically isolates the active wire and the ground electrode. In other aspects according to the present disclosure, the hypotube electrically isolates the active pin and the ground electrode when the electrode assembly is engaged within the distal end of the electrosurgical pencil. In yet other aspects according to the present disclosure, the stamped electrically conductive material is configured to wrap around the insulative core and the first hypotube. In still other aspects according to the present disclosure, a rivet secures the ground electrode atop the insulative core and the first hypotube.

In aspects according to the present disclosure, a tensioning mechanism operably engages the active pin and is configured to tension the active wire upon actuation thereof. In other aspects according to the present disclosure, the tensioning mechanism includes a nut affixed to the insulative material that is configured to mechanically interface with a thread on the active pin such that rotation of the activation pin provides tension to the active wire.

Provided in accordance with other aspects of the present disclosure is an electrode assembly for an electrosurgical pencil that includes an insulative core configured to support an active wire around at least a portion of a peripheral surface thereof, the active wire electrically coupled to an active pin adapted for insertion within a distal end of an electrosurgical pencil. A ground electrode is made from a stamped electrically conductive material and is configured to wrap around a top surface of the insulative core and at least a portion of the ground electrode and is adapted for insertion within the distal end of the electrosurgical pencil. A first hypotube is disposed atop the top surface of the insulative core and extends along a length thereof between the ground electrode and the insulative core. The first hypotube encapsulates the active wire to insulate the active wire from the ground electrode along a length thereof. The first hypotube includes an opening at a distal end thereof configured to expose and guide the active wire into a cuff defined in a bottom surface of the insulative core. A second hypotube operably engages a proximal end of the insulative material and is configured to at least partially encapsulate the active pin.

In aspects according to the present disclosure, an insulative material is disposed between the active pin and the ground electrode and is configured to at least partially encapsulate and electrically isolate the active pin from the ground electrode along a partial length thereof. In other aspects according to the present disclosure, a leading edge of the ground electrode is spaced from the peripheral surface of the insulative core to define a gap therebetween configured to electrically isolate the active wire and the ground electrode during activation to avoid arcing.

In aspects according to the present disclosure, the insulative core is made from ceramic. In other aspects according to the present disclosure, the active wire is made from tungsten or stainless steel. In yet other aspects according to the present disclosure, the ground electrode extends along a length of the insulative core.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

DETAILED DESCRIPTION

Figure 1:
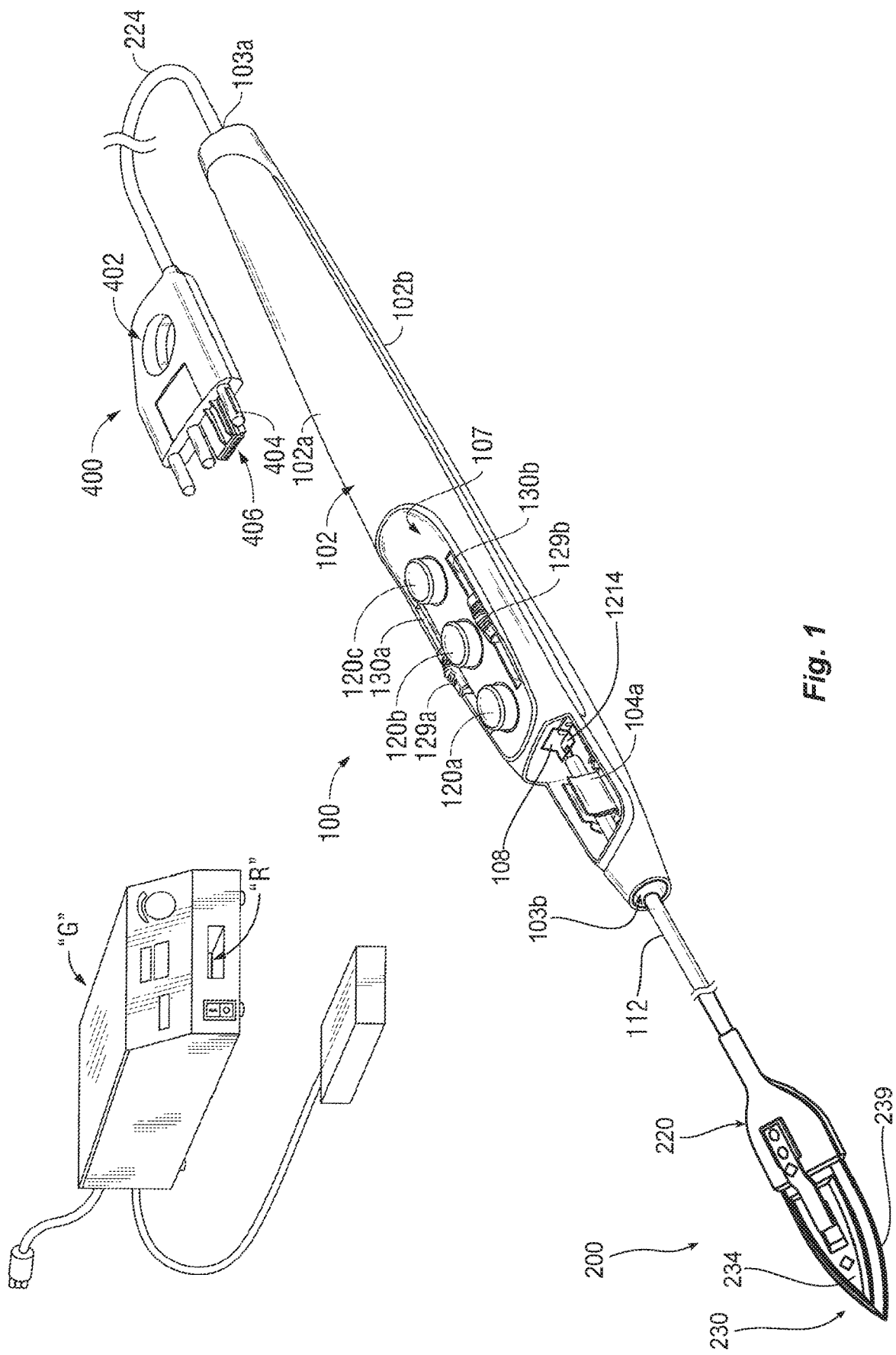
FIG. 1 is a perspective view of a commonly-owned electrosurgical system including an electrosurgical pencil including a housing having a shaft extending therefrom with an end effector attached to a distal end thereof, the end effector configured for bipolar resection in accordance with an embodiment of the present disclosure.

Particular embodiments of the presently disclosed electrosurgical pencil configured for bipolar resection are described in detail with reference to the drawing figures wherein like reference numerals identify similar or identical elements. As used herein, the term "distal" refers to that portion which is further from the user while the term "proximal" refers to that portion which is closer to the user or clinician. The term "leading edge" refers to the most forward edge with respect to the direction of travel while the term "trailing edge" refers to the edge opposite the leading edge with respect to the direction of travel.

FIG. 1 sets forth a perspective view of an electrosurgical system including a commonly-owned electrosurgical pencil 100 constructed for bipolar resection in accordance with one embodiment of the present disclosure. While the following description is directed towards electrosurgical pencils for bipolar resection, the features and concepts (or portions thereof) of the present disclosure may be applied to any electrosurgical type instrument, e.g., forceps, suction coagulators, vessel sealers, wands, etc. The construction, functionality and operation of electrosurgical pencils, with respect to use for bipolar resection, is described herein. Further details of the electrosurgical pencil are provided in commonly-owned U.S. patent application Ser. No. 16/540, 593 filed Aug. 14, 1019 by Baril et al., the entire contents of which being incorporated by reference herein.

The general functions and elements of the prior art, commonly-owned electrosurgical pencil 100 are discussed herein with reference to FIGS. 1-4 of the above-mentioned prior disclosure U.S. patent application Ser. No. 16/540,593.

Electrosurgical pencil 100 includes an elongated housing 102 having a top-half shell portion 102a and a bottom-half shell portion 102b. The elongated housing 102 includes a distal opening 103b, through which a shaft 112 of an end effector assembly 200 extends, and a proximal opening 103a, through which connecting wire 224 (see FIG. 1) extends. Top-half shell portion 102a and bottom-half shell portion 102b may be bonded together using any suitable method, e.g., sonic energy, adhesives, snap-fit assemblies, etc.

Electrosurgical pencil 100 further includes a shaft receptacle 104 disposed at a distal end 103b of housing 102 that is configured to receive the shaft 112 of the selectively removable end effector assembly 200. Electrode assembly 200 is configured to electrically connect to generator "G" through various electrical conductors (not shown) formed in the shaft 112, elongated housing 102, connecting wire 224 and plug assembly 400. Generator "G" may be incorporated into the elongated housing 102 and powered by an internal energy supply, e.g., battery or other energy storage device, fuel cell or other energy generation device or any other suitable portable power source.

Shaft 112 is selectively retained by shaft receptacle 104 disposed in housing 102. Shaft 112 may include a plurality of conductive traces or wires (not shown) along the length of the shaft 112. The conductive traces or wires may be fabricated from a conductive type material, such as, for example, stainless steel, or shaft may be coated with an electrically conductive material. Shaft receptacle 104 is fabricated from electrically conductive materials or includes electrically conductive contacts configured to couple with the plurality of conductive traces or wires of the shaft 112. Shaft receptacle 104 is electrically connected to voltage divider network 127 (FIGS. 2 and 4) as explained in more detail below. Conductive traces or wires of the shaft 112 electrically connect to the electrode assembly 200 as explained in more detail below.

As seen in FIG. 1, electrosurgical pencil 100 may be coupled to a conventional electrosurgical generator "G" via a plug assembly 400 (see FIG. 3), as will be described in greater detail below.

For the purposes herein, the terms "switch" or "switches" includes electrical actuators, mechanical actuators, electromechanical actuators (rotatable actuators, pivotable actuators, toggle-like actuators, buttons, etc.) or optical actuators.

Figure 2:
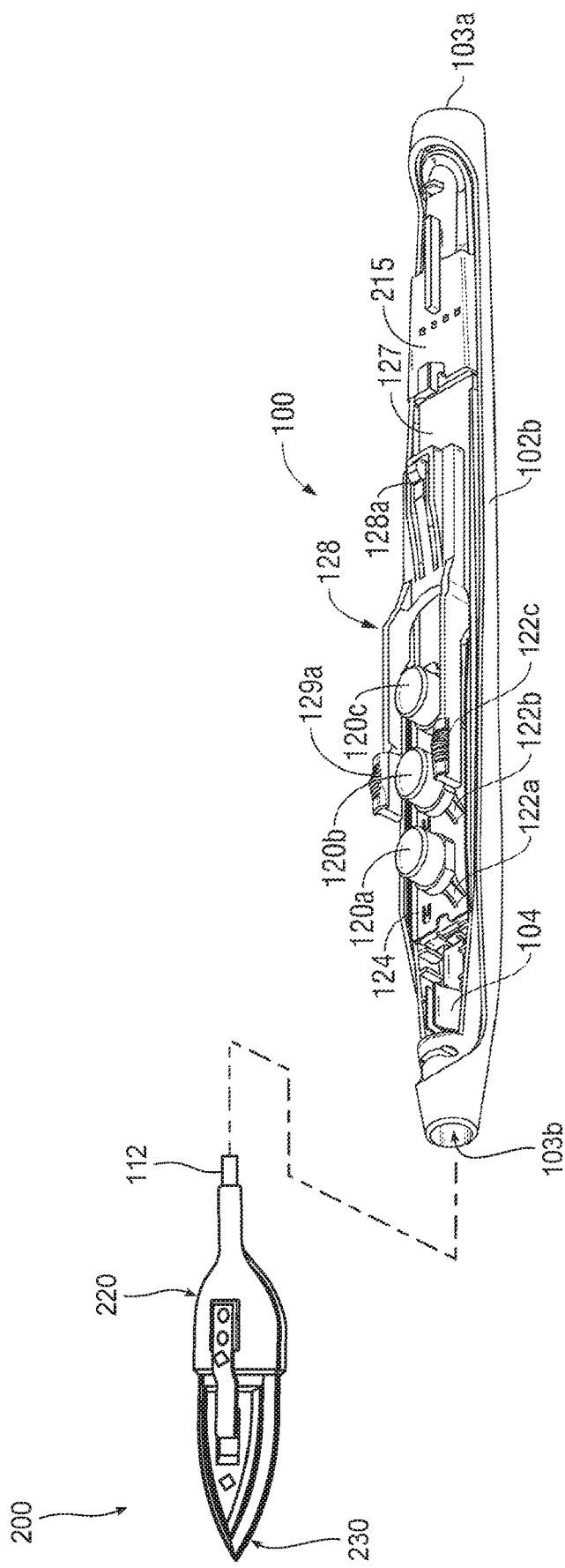
FIG. 2 is a front, top perspective view of the electrosurgical pencil of FIG. 1, with a top-half shell of the housing removed.

Electrosurgical pencil 100 includes one or more activation switches, and may include three activation switches 120a-120c, each of which extends through top-half shell portion 102a of elongated housing 102. Each activation switch 120a-120c is operatively supported on a respective tactile element 122a-122c provided on a switch plate 124, as illustrated in FIG. 2. Each activation switch 120a-120c controls the transmission of RF electrical energy supplied from generator "G" to bipolar electrodes 138 on electrode face 105 of electrode body 112.

More particularly, switch plate 124 is positioned on top of a voltage divider network 127 (hereinafter "VDN 127") such that tactile elements 122a-122c are operatively associated therewith. VDN 127 (e.g., here shown in FIG. 2 as a film-type potentiometer) forms a switch closure. For the purposes herein, the term "voltage divider network" relates to any known form of resistive, capacitive or inductive switch closure (or the like) which determines the output voltage across a voltage source (e.g., one of two impedances) connected in series. A "voltage divider" as used herein relates to a number of resistors connected in series which are provided with taps at certain points to make available a fixed or variable fraction of the applied voltage. Further details of electrosurgical pencil control are provided in above-mentioned U.S. patent application Ser. No. 16/540, 593.

Figure 3:
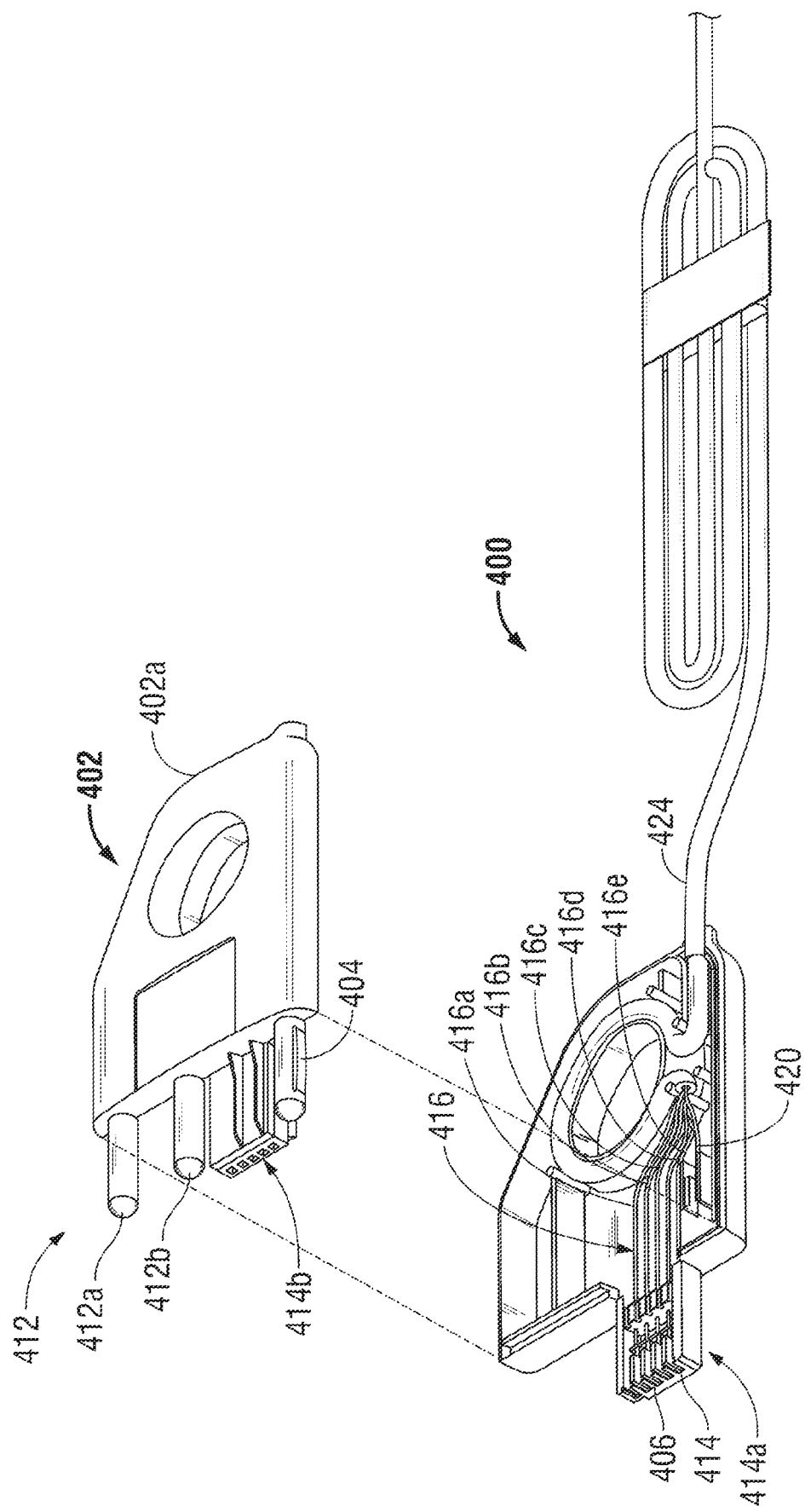
FIG. 3 is a perspective view of the plug assembly of FIG. 1, with a top-half shell section removed therefrom.

In use, depending on which activation switch 120a-120c is depressed a respective tactile element 122a-122c is pressed into contact with VDN 127 and a characteristic signal is transmitted to electrosurgical generator "G" via control wires 416 (see FIG. 3). In one embodiment, three control wires 416a-416c (one for each activation switch 120a-120c, respectively) are provided. Control wires 416a-416c are electrically connected to switches 120a-120c via a control terminal 215 (see FIG. 2) which is operatively connected to VDN 127. By way of example only, electrosurgical generator "G" may be used in conjunction with the device wherein generator "G" includes a circuit for interpreting and responding to the VDN 127 settings.

Activation switches 120a, 120b, 120c are configured and adapted to control the mode and/or "waveform duty cycle" to achieve a desired surgical intent. For example, a first activation switch 120a can be set to deliver a characteristic signal to electrosurgical generator "G" which, in turn, transmits a duty cycle and/or waveform shape that produces a first desirable resection effect. Meanwhile, second activation switch 120b can be set to deliver a characteristic signal to electrosurgical generator "G" which, in turn, transmits a duty cycle and/or waveform shape that produces a second desirable resection effect.

Finally, third activation switch 120c can be set to deliver a characteristic signal to electrosurgical generator "G" which, in turn, transmits a duty cycle and/or waveform shape that produces a third electrosurgical effect/function. Desirable resection effects may include a mode for bipolar coagulation and/or cauterization with an undeployed blade, a mode for bipolar resection with a partially deployed blade, a mode for bipolar resection with a fully deployed blade, a mode for monopolar resection and a mode for resection with blended energy delivery (monopolar and bipolar modes), as will be described in greater detail hereinbelow.

As seen in FIG. 3, fourth and fifth wires (e.g., first RF line 416d and second RF line 416e) are provided and electrically connect to respective active and return electrodes 239, 234 of the end effector assembly 200 (See FIG. 1). Since first RF line 416d and second RF line 416e are directly connected to the end effector assembly 200, first RF line 416d and second RF line 416e bypass the VDN 127 and are isolated from VDN 127 and control wires 416a-416c. By directly connecting the first RF line 416d and second RF line 416e to the end effector assembly 200 (as explained in more detail below) and isolating the VDN 127 from the RF energy transmission, the electrosurgical current does not flow through VDN 127. This, in turn, increases the longevity and life of VDN 127 and/or activation switches 120a, 120b, 120c.

Figure 4:
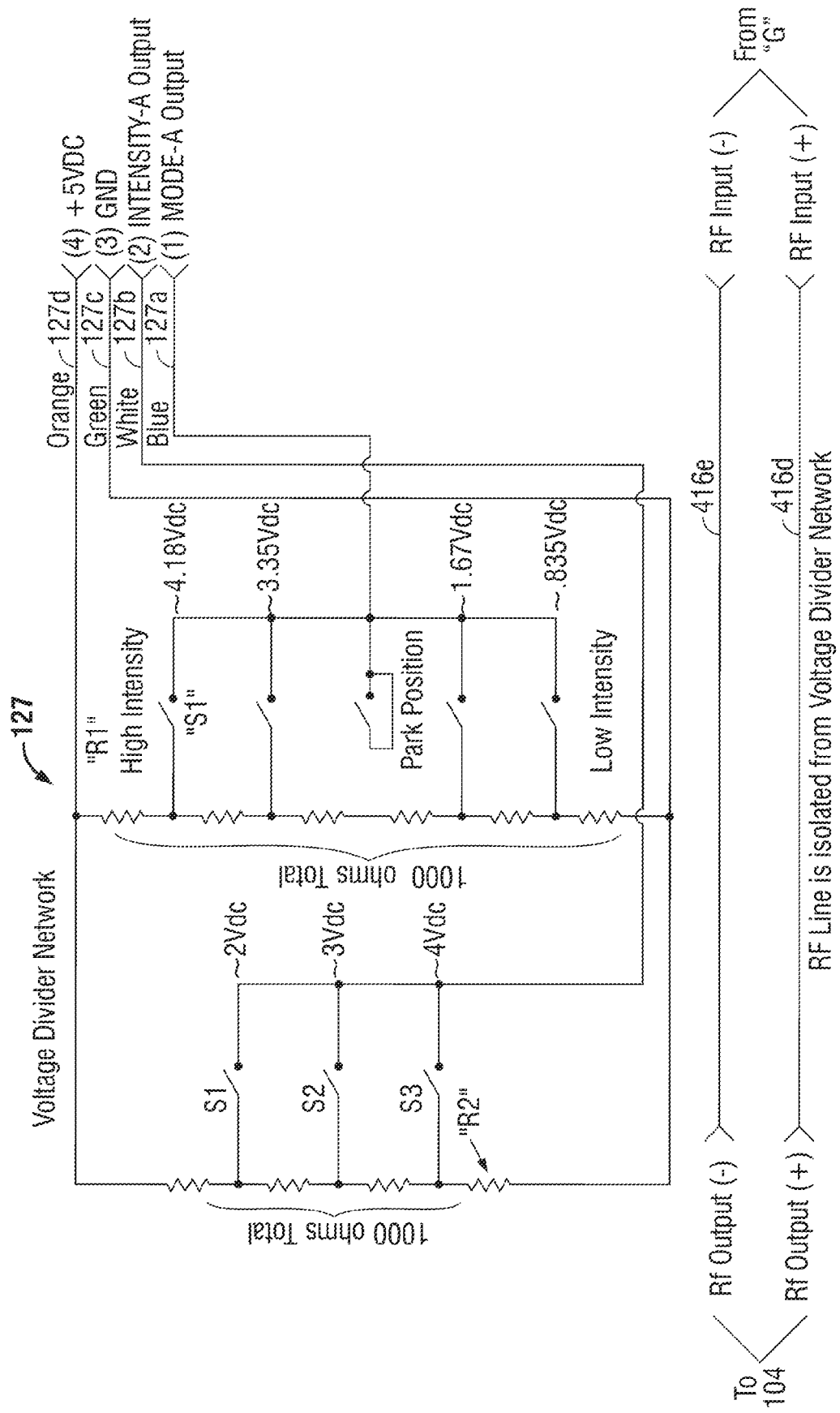
FIG. 4 is a schematic illustration of a voltage divider network for use with the electrosurgical pencil of FIG. 1 and embodiments according to the present disclosure.

With reference to FIG. 4, VDN 127 is shown and includes a first transmission line 127a configured to operate the various modes of electrosurgical pencil 100; a second transmission line 127b configured to operate the various intensities of electrosurgical pencil 100; a third transmission line 127c configured to function as a ground for VDN 127; and a fourth transmission line 127d which transmits up to about +5 volts to VDN 127.

First RF line 416d and second RF line 416e are isolated from or otherwise completely separate from VDN 127. In particular, first RF line 416d and second RF line 416e extends directly from the RF input or generator "G" to the active electrode 239 and return electrodes 234a, 234b of the end effector assembly 200 as explained in more detail below.

By way of example only, VDN 127 may include a plurality of resistors "R1" (e.g., six resistors), connected in a first series between third transmission line 127c and fourth transmission line 127d. The first series of resistors "R1" may combine to total about 1000 ohms of resistance. The first series of resistors "R1" are each separated by a first set of switches "S1". Each switch of the first set of switches "S1" may be electrically connected between adjacent resistors "R1" and first transmission line 127a of VDN 127. In operation, depending on which switch or switches of the first set of switches "S1" is/are closed, a different mode of operation for electrosurgical pencil 100 is activated.

Resection may be performed with electrosurgical energy including waveforms having a duty cycle from about 10% to about 100%. The dual effect of coagulating and cauterizing, as described herein, may be performed with a waveform having a duty cycle from about 10% to about 100%. To increase the depth of coagulation may require a waveform with a duty cycle from about 50% to 100%. It is important to note that these percentages are approximated and may be customized to deliver the desired surgical effect for various tissue types and characteristics.

In one embodiment, the waveforms provided to the bipolar electrosurgical pencil 100 may be dynamically controlled by the generator "G". For example, the mode of operation provided by switches S1, S2, S3 may indicate a range of operation for the generator "G". Generator "G" provides a waveform within the specified range of operation wherein the waveform is dynamically changed based on a parameter, wherein the parameter may be related to one of energy delivery, the target tissue and the duration of energy delivery. The parameter may be obtained from a source external to the generator "G", such as, a measured parameter or clinician provided parameter, or the parameter may include an internal parameter obtained, measured or determined by the generator "G".

As seen throughout FIG. 2, electrosurgical pencil 100 further includes an intensity controller 128 slidingly supported on or in elongated housing 102. Intensity controller 128 may be configured to function as a slide potentiometer, sliding over and along VDN 127 wherein the distal-most position corresponds to a relative high intensity setting, the proximal-most position corresponds to a low intensity settings with a plurality of intermediate positions therebetween. As can be appreciated, the intensity settings from the proximal end to the distal end may be reversed, e.g., high to low.

The intensity settings are typically preset and selected from a look-up table based on a choice of electrosurgical instruments/attachments, desired surgical effect, surgical specialty and/or surgeon preference, the type of end effector assembly 200 and the arrangement of the active and return electrodes 239, 234. The selection of the end effector assembly 200, the intensity setting and duty cycle determines the surgical effect. The settings may be selected manually by the user or automatically. For example, the electrosurgical generator "G" may automatically determine the type of end effector assembly 200 and a predetermined intensity value may be selected and subsequently adjusted by the user or the electrosurgical generator "G".

Turning now to FIG. 3, a detailed discussion of plug assembly 400 is provided. Plug assembly 400 includes a housing portion 402 and a connecting wire 424 that electrically interconnects the housing portion 402 and the control terminal 215 in the electrosurgical pencil 100 (see FIG. 2). Housing portion 402 includes a first half-section 402a and a second half-section 402b operatively engageable with one another, e.g., via a snap-fit engagement. First half-section 402a and second half-section 402b are configured and adapted to retain a common power pin 404 and a plurality of electrical contacts 406 therebetween.

Common power pin 404 of plug assembly 400 extends distally from housing portion 402 at a location between first half-section 402a and second half-section 402b. Common power pin 404 may be positioned to be off center, i.e., closer to one side edge of housing portion 402 than the other. Plug assembly 400 further includes at least one a pair of position pins 412 also extending from housing portion 402. Position pins 412 may be positioned between the first half-section 402a and the second half-section 402b of housing portion 402 and are oriented in the same direction as common power pin 404.

A first position pin 412a is positioned in close proximity to a center of housing portion 402 and a second position pin 412b is positioned to be off center and in close proximity to an opposite side edge of housing portion 402 as compared to common power pin 404. First position pin 412a, second position pin 412b and common power pin 404 may be located on housing portion 402 at locations which correspond to pin receiving positions (not shown) of a connector receptacle "R" of electrosurgical generator "G" (see FIG. 1).

Plug assembly 400 further includes a prong 414 extending from housing portion 402. In particular, prong 414 includes a body portion 414a extending from second half-section 402b of housing portion 402 and a cover portion 414b extending from first half-section 402a of housing portion 402. In this manner, when the first half-section 402a and the second half-section 402b are joined to one another, cover portion 414b of prong 414 encloses the body portion 414a. Prong 414 may be positioned between common power pin 404 and first position pin 412a. Prong 414 is configured and adapted to retain electrical contacts 406 therein such that a portion of each electrical contact 406 is exposed along a front or distal edge thereof. While five electrical contacts 406 are shown, any number of electrical contacts 406 can be provided, including and not limited to two, six and eight. Prong 414 may be located on housing portion 402 at a location that corresponds to a prong receiving position (not shown) of connector receptacle "R" of electrosurgical generator "G" (see FIG. 1).

Since prong 414 extends from second half-section 402b of housing portion 402, housing portion 402 of plug assembly 400 will not enter connector receptacle "R" of electrosurgical generator "G" unless housing portion 402 is in a proper orientation. In other words, prong 414 functions as a polarization member. This ensures that common power pin 404 is properly received in connector receptacle "R" of electrosurgical generator "G".

Connecting wire 424 includes a power supplying wire 420 electrically connected to common power pin 404, control wires 416a-416c electrically connected to a respective electrical contact 406, and first RF line 416d and second RF line 416e electrically connected to a respective electrical contact 406.

Turning to FIG. 5A-5D, the presently disclosed end effector assembly 1200 may be used with electrosurgical pencil 100 and includes a shaft 1212 having a proximal portion 1214 configured to mechanically and electrically engage shaft receptacle 104 (See FIG. 1). Shaft 1212 and shaft receptacle 104 are configured to provide a plurality of suitable electrical connections therebetween to facility the delivery of electrosurgical energy from the electrosurgical generator "G" (See FIG. 1) to an active electrode or active wire 1225 and return or ground electrode 1217.

A proximal or active pin 1214 of shaft 1212 is inserted into distal opening 103*b* of the elongated housing 102 to engage shaft receptacle 104. Active pin 1214 electrically couples to active wire 1225 at a connection point 1214*a* at a distal end thereof as explained in more detail below. Shaft receptacle 104 is configured to mechanically and electrically couple the shaft 1212 to the elongated housing 102. Electrical connections may include one or more electrical connectors 108 (or electrical connector pairs—not shown) disposed in housing 102 that connect to the active pin 1214 and one or more electrical connectors or conductive rings 104*a* that connect to the ground electrode 1217 upon engagement of the shaft 1212 into shaft receptacle 104. Shaft 1212 and shaft receptacle 104 may include a locking device, such as, for example, a shaft locking pin that slides into and engages a shaft locking pin receptacle (not explicitly shown). Any suitable securing and/or locking apparatus may be used to releasably secure the shaft 1212 to the elongated housing 102. As described herein, the shaft 1212 is interchangeable with the elongated housing 102. In other embodiments, shaft 1212 is integrated into the elongated housing 102 and is not replaceable.

Turning back to FIGS. 5A and 5B, electrode assembly 1200 includes an insulative support 1240, e.g., a ceramic core, configured to support ground electrode 1217 along a length thereof and active wire 1225, e.g., a tungsten wire, around a portion of a peripheral surface thereof as explained in more detail below.

Figure 5A:
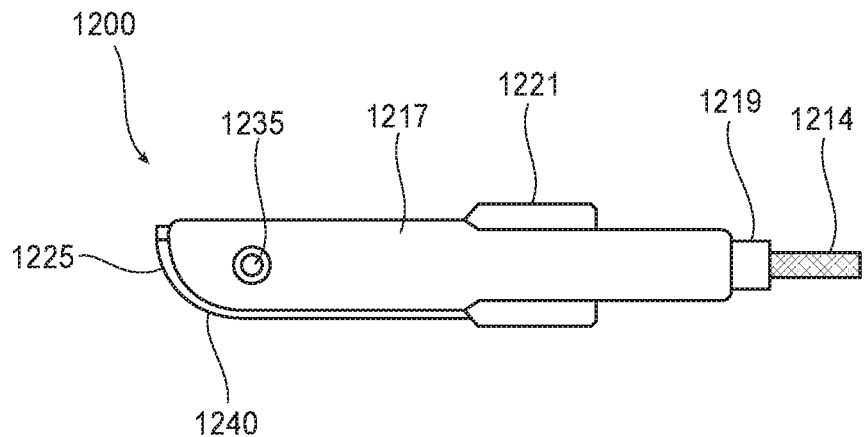
FIG. 5A is an enlarged, side view of one embodiment of an end effector assembly according to the present disclosure.
Figure 5B:
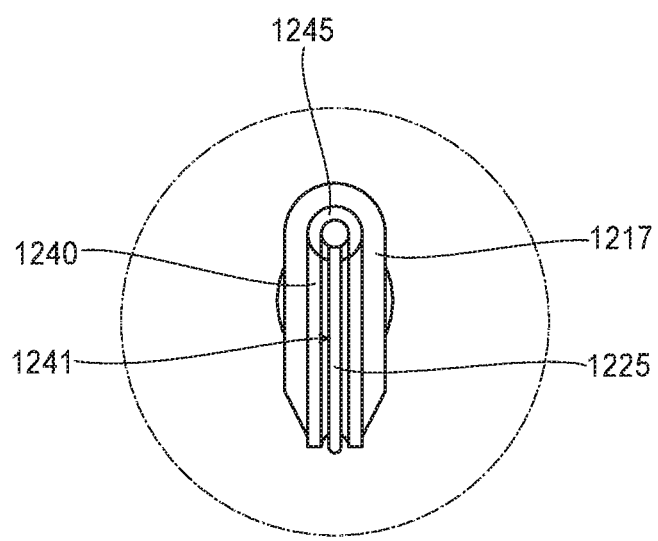
FIG. 5B is an enlarged, front view of the end effector assembly of FIG. 5A.
Figure 5C:
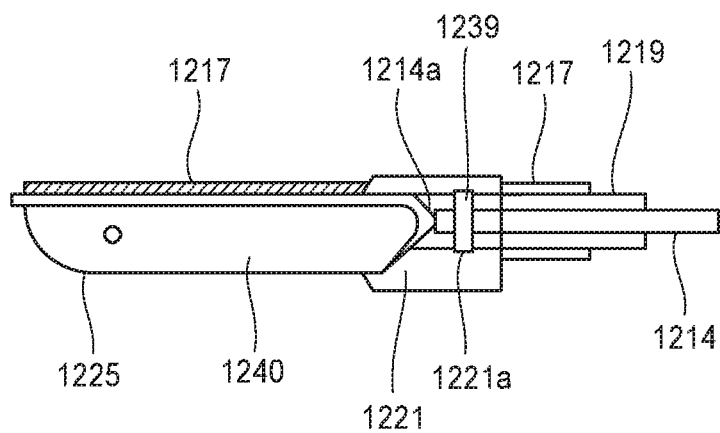
FIG. 5C is an enlarged, sectional view of the end effector assembly of FIG. 5A.

A hypotube 1245 is configured to sit atop the ceramic core 1240 and extend from a proximal end of the ceramic core proximate the electromechanical connection point 1214*a* of the active pin 1214 and the active wire 1225 and extend distally along the length thereof. The hypotube 1245 is configured to encapsulate the active wire 1225 and isolate the active wire 1225 from the ground electrode 1217 (FIGS. 5B and 5D).

Ground electrode 1217 may be formed from a single piece of stamped material and formed around the hypotube 1245 and the ceramic core 1240. The stamped ground electrode 1217 may be formed in a round or box-like manner and may include a series of mechanical interfaces, e.g., a rivet 1235, to secure the stamped ground electrode 1217 around the ceramic core 1240 and/or hypotube 1245. The ground electrode 1217 may include a bend area 1217*a* to facilitate formation around the hypotube 1245 and ceramic core 1240 (FIG. 5D).

As mentioned above, active wire 1225 electrically couples to active pin 1214 which, in turn, electrically couples to contact 108 disposed in housing 102 when the electrode assembly 1200 is engaged to electrosurgical pencil 100. The active wire 1225 is fed from active pin 1214, through hypotube 1245 to electrically isolate the active wire 1225 from the ground electrode 1217 and out through a distal opening 1244 defined in hypotube 1245 to engage the outer peripheral surface of the ceramic core 1240. Ceramic core 1240 includes a cuff 1241 (FIGS. 5B and 5D) defined therealong to house and seat the active wire 1225 as the active wire 1225 extends proximally back to the electrical connection point 1214*a* with the active pin 1214.

Figure 5D:
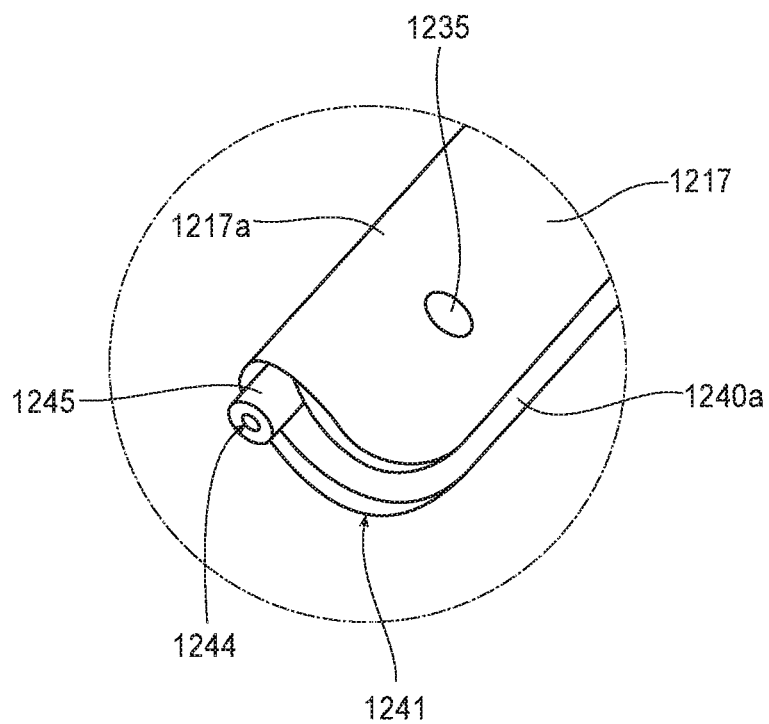
FIG. 5D is a greatly-enlarged, end perspective view of the distal end of the end effector assembly of FIG. 5A.

As shown in FIG. 5D, ground electrode 1217 only partially wraps about ceramic core 1240 to define an electrical isolation gap 1240*a* between an outer edge of the ceramic core 1240 and the leading edge of the ground electrode 1217. Gap 1240*a* avoids arcing between electrical potentials during activation.

Turning back to FIGS. 5A and 5C, electrode assembly 1200 includes an insulative plastic 1221 disposed between the ground electrode 1217, the active wire 1225 and active pin 1214 that is configured to insulate the electrodes 1225, 1217 during activation. A second hollow tube or hypotube 1219 encapsulates a portion of the active wire 1225 and further insulates the active wire 1225 from the ground electrode 1217 as the active wire 1225 and active pin 1214 extend proximally towards housing 102. Hypotube 1219 may be configured to mechanically engage a corresponding mechanical connection (not shown) proximate of shaft receptacle 104 to facilitate secure engagement of the end effector assembly 1200 therein.

A tensioning mechanism (FIG. 5C) is disposed the ceramic core 1240 at a distal end of the active pin 1214. The tensioning mechanism includes a nut-like mechanical interface 1239 secured at a connection point 1221*a* within the insulative plastic 1221 (or some other point of securement in the electrode assembly 1200). Nut 1239 is configured to threadably engage the distal end of the active pin 1214 such that the active pin 1214 may be selectively rotated during assembly to retract the active wire 1225 and provide additional tension to the active wire 1225 to properly seat the active wire 1225 within cuff 1241 of ceramic core 1240 as needed.

Ground electrode 1217 extends proximate the proximal end of the electrode assembly 1200 for connection to corresponding connector 104*a* disposed in distal opening 103*b* upon engagement of the end effector assembly 1200 with the housing 102 for ultimate connection to a common ground. Shaft receptacle 104 may include one or more mechanical interfaces to facilitate engagement of the end effector assembly 1200 with housing 102. Contact 108 operably and electrically couples to active pin 1214 which, in turn, electrically couples to one or more switches 120*a*, 120*b*, 120*c* (See FIG. 2) disposed on housing 102 used to activate the generator "G" to energize the active wire 1225 and ground electrode 1217 in a bipolar manner. The variously described switches 120*a*-120*c* with respect to FIGS. 1-4 may also be utilized along with the intensity controllers 129*a*, 129*b* associated therewith.

By providing a single pole (or active wire 1225) connection to the activation contact 108 coupled with an in-line connection to the ground electrode 1217, the overall profile of the pencil 100 is significantly reduced compared to a two-pole configuration providing greater visibility to the surgical site.

As mentioned above, the active wire 1225 may be made from any suitable conductive material such as tungsten, surgical stainless steel, etc. Tungsten is particularly favored since various geometries for the active wire 1225 may be easily 3D printed providing additional robustness over traditional wire designs while offering an optimized surface area to increase cutting efficiency. Moreover a sheet including a plurality of tungsten wires 1225 may be 3D printed to facilitate the manufacturing process. Moreover, multiple geometries may be easily integrated with the mating geometry of the various mechanical interfaces staying the same. The exposed edge (not explicitly shown) of active wire 1225 is configured for cutting and is designed to concentrate electrosurgical energy to increase cutting efficiency.

The ground electrode 1217 may be made from a conductive material and insulated from the respective active wire 1225 via plastic body 1221 and/or hypotubes 1219, 1245. During activation, the return electrode 1217 provides a return path for the electrosurgical energy from the active wire 1225 such that the circuit is completed.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. For example, the knife body and tube do not necessarily have to be made from the exact same materials. Similar materials, or any two materials that can be welded together to allow for a durable weld joint could be used.

The invention claimed is:

1. An electrode assembly for an electrosurgical pencil, comprising:

an insulative core configured to support an active wire around at least a portion of a peripheral surface of a distal end of the insulative core, the active wire electrically coupled to an active pin adapted for insertion within a distal end of an electrosurgical pencil;

a ground electrode operably coupled about the insulative core and adapted for insertion within the distal end of the electrosurgical pencil;

an insulative material disposed between the active pin and the ground electrode and configured to at least partially encapsulate and electrically isolate the active pin from the ground electrode;

a first hypotube disposed atop the insulative core and extending between the ground electrode and the insulative core, the first hypotube encapsulating the active wire to insulate the active wire from the ground electrode; and a second hypotube operably engaged to a proximal end of the insulative material and configured to at least partially encapsulate the active pin.

2. The electrode assembly of claim 1, wherein the insulative core includes a cuff and the active wire is seated within the cuff.

3. The electrode assembly of claim 2, wherein the first hypotube defines an opening at a distal end of the first hypotube, the opening configured to expose and guide the active wire into the cuff defined in the insulative core.

4. The electrode assembly of claim 1, wherein a leading edge of the ground electrode is spaced from the peripheral surface of the insulative core to define a gap between the leading edge of the ground electrode and the peripheral surface of the insulative core, the gap configured to electrically isolate the active wire and the ground electrode during activation to avoid arcing.

5. The electrode assembly of claim 1, wherein the insulative core is made from ceramic.

6. The electrode assembly of claim 1, wherein the active wire is made from tungsten or stainless steel.

7. The electrode assembly of claim 1, wherein the insulative material electrically isolates the active wire and the ground electrode.

8. The electrode assembly of claim 1, wherein the second hypotube electrically isolates the active pin and the ground electrode when the electrode assembly is engaged within the distal end of the electrosurgical pencil.

9. The electrode assembly of claim 1, wherein the ground electrode is made from a stamped electrically conductive material.

10. The electrode assembly of claim 9, wherein the stamped electrically conductive material is configured to wrap around the insulative core and the first hypotube.

11. The electrode assembly of claim 10, wherein a rivet secures the ground electrode atop the insulative core and the first hypotube.

12. The electrode assembly of claim 1, further comprising a tensioning mechanism operably engaged to the active pin and configured to tension the active wire.

13. The electrode assembly of claim 12, wherein the tensioning mechanism includes a nut affixed to the insulative material that is configured to mechanically interface with a thread on the active pin such that rotation of the activation pin provides tension to the active wire.

14. An electrode assembly for an electrosurgical pencil, comprising:

an insulative core configured to support an active wire around at least a portion of a peripheral surface of a distal end of the insulative core, the active wire electrically coupled to an active pin adapted for insertion within a distal end of an electrosurgical pencil;

a ground electrode made from a stamped electrically conductive material and configured to wrap around a top surface of the insulative core, at least a portion of the ground electrode adapted for insertion within the distal end of the electrosurgical pencil;

a first hypotube disposed atop the top surface of the insulative core and extending between the ground electrode and the insulative core, the first hypotube encapsulating the active wire to insulate the active wire from the ground electrode, the first hypotube including an opening at a distal end of the first hypotube, the opening configured to expose and guide the active wire into a cuff defined in a bottom surface of the insulative core; and a second hypotube configured to at least partially encapsulate the active pin.

15. The electrode assembly of claim 14, further comprising an insulative material disposed between the active pin and the ground electrode and configured to at least partially encapsulate the active pin and electrically isolate the active pin from the ground electrode.

16. The electrode assembly of claim 14, wherein a leading edge of the ground electrode is spaced from the peripheral surface of the insulative core to define a gap between the leading edge of the ground electrode and the peripheral surface of the insulative core, the gap configured to electrically isolate the active wire and the ground electrode during activation to avoid arcing.

17. The electrode assembly of claim 14, wherein the insulative core is made from ceramic.

18. The electrode assembly of claim 14, wherein the active wire is made from tungsten or stainless steel.

19. The electrode assembly of claim 14, wherein the ground electrode extends along a length of the insulative core.

20. An electrode assembly for an electrosurgical pencil, comprising:

an insulative core having a peripheral surface configured to support an active wire, the active wire electrically coupled to an active pin adapted for insertion within a distal end of an electrosurgical pencil;

a tensioning mechanism operably engaged to the active pin and configured to tension the active wire;

a ground electrode operably coupled to the insulative core and adapted for insertion within the distal end of the electrosurgical pencil;

an insulative material disposed between the active pin and the ground electrode and configured to at least partially encapsulate the active pin and electrically isolate the active pin from the ground electrode;

a first hypotube disposed between the ground electrode and the insulative core, the first hypotube encapsulating the active wire to insulate the active wire from the ground electrode; and a second hypotube operably engaged to a proximal end of the insulative material and configured to at least partially encapsulate the active pin.

* * * * *